United States Patent
Travis

(10) Patent No.: US 11,033,527 B2
(45) Date of Patent: Jun. 15, 2021

(54) NON-HORMONAL TREATMENT OF THE GENITOURINARY SYNDROME OF MENOPAUSE

(71) Applicant: IMMUGEN PHARMA LLC, South Miami, FL (US)

(72) Inventor: Craig R. Travis, South Miami, FL (US)

(73) Assignee: IMMUGEN PHARMA LLC, South Miami, FL (US)

(*) Notice: Subject to any disclaimer, the term of this patent is extended or adjusted under 35 U.S.C. 154(b) by 126 days.

(21) Appl. No.: 16/269,719

(22) Filed: Feb. 7, 2019

(65) Prior Publication Data

US 2019/0240190 A1 Aug. 8, 2019

Related U.S. Application Data

(60) Provisional application No. 62/627,430, filed on Feb. 7, 2018.

(51) Int. Cl.
*A61K 31/352* (2006.01)
*A61P 15/02* (2006.01)
*A61K 31/565* (2006.01)

(52) U.S. Cl.
CPC .......... *A61K 31/352* (2013.01); *A61K 31/565* (2013.01); *A61P 15/02* (2018.01)

(58) Field of Classification Search
CPC ...... A61K 31/352; A61K 31/565; A61P 15/02
See application file for complete search history.

(56) References Cited

U.S. PATENT DOCUMENTS

| | | | |
|---|---|---|---|
| 6,274,635 | B1 | 8/2001 | Travis |
| 6,541,510 | B2 | 4/2003 | Travis |
| 8,586,767 | B2 | 11/2013 | Travis |
| 9,173,867 | B2 | 11/2015 | Travis |
| 2002/0137802 | A1 | 9/2002 | Travis |
| 2003/0232101 | A1 | 12/2003 | Travis |
| 2004/0138315 | A1 | 7/2004 | Travis |
| 2004/0242870 | A1 | 12/2004 | Travis |

(Continued)

FOREIGN PATENT DOCUMENTS

| | | |
|---|---|---|
| AU | 2001296402 A1 | 4/2002 |
| AU | 2003263895 A | 12/2003 |

(Continued)

OTHER PUBLICATIONS

Amabebe, et al.: "The Vaginal Microenvironment: The Physiologic Role of Lactobacilli", Frontiers in Medicine, vol. 5, Jun. 13, 2018.

(Continued)

*Primary Examiner* — San Ming R Hui
(74) *Attorney, Agent, or Firm* — Fox Rothschild LLP

(57) ABSTRACT

Methods of treating the genitourinary syndrome of menopause (GSM) and modulating expression of genes involved in the GSM in an individual include administering compound L759,633 or compound JWH-133, both selective ligands for the endocannabinoid receptor type 2 (CB2). These compounds and compositions containing these compounds can be used as a non-hormonal alternative to hormones such as estrogen and ospemiphene for the treatment of the GSM and in particular, vaginal atrophy (VVA).

14 Claims, 1 Drawing Sheet

(56) References Cited

U.S. PATENT DOCUMENTS

| | | | |
|---|---|---|---|
| 2007/0179135 | A1 | 8/2007 | Travis |
| 2008/0108647 | A1 | 5/2008 | Travis |

FOREIGN PATENT DOCUMENTS

| | | | | |
|---|---|---|---|---|
| AU | 2004202466 | A1 | 7/2004 | |
| WO | WO2004016254 | A2 | 2/2004 | |
| WO | WO-2012098090 | A1 * | 7/2012 | ............... A61P 15/00 |
| ZA | 200107773 | B | 4/2003 | |

OTHER PUBLICATIONS

Becknell, et al.: "A Review of Ribonuclease 7's Structure, Regulation, and Contributions to Host Defense", International Journal of Molecular Sciences, vol. 17, Mar. 22, 2016.

Calippe, et al.: "Complement Factor H Inhibits CD47-Mediated Resolution of Inflammation", Immunity, vol. 46, Feb. 21, 2017.

Candi, et al.:"Transglutaminase Cross-linking Properties of the Small Proline-rich 1 Family of Cornified Cell Envelope Proteins", The Journal of Biological Chemistry, vol. 274, Mar. 12, 1999.

Analysis and Writing Committee: "Menopausal hormone use and ovarian cancer risk: individual participant meta-analysis of 52 epidemiological studies", Lancet, vol. 385, May 9, 2015.

Cotreau, et al.: "A study of 17ß-estradiol-regulated genes in the vagina of postmenopausal women with vaginal atrophy", Maturitas, vol. 58, Sep. 17, 2007.

Das, et al.: "Cannabinoid ligand-receptor signaling in the mouse uterus", Proc. Natl. Acad. Sci. USA, vol. 92, May 1995.

Gammon, et al.: "Regulation of Gonadotropin-Releasing Hormone Secretion by Cannabinoids", Endocrinology, vol. 146, Jul. 14, 2005.

Gerber, et al.: "Systematic Identification and Characterization of Novel Human Skin-Associated Genes Encoding Membrane and Secreted Proteins", Plos One, vol. 8, Jun. 20, 2013.

Gipson, et al.: "Mucin Genes Expressed by Human Female Reproductive Tract Epithelia", Biology of Reproduction, vol. 56, 199T.

Goldstein, MD, et al.: "Multidisciplinary Overview of Vaginal Atrophy and Associated Genitourinary Symptoms in Postmenopausal Women", Sexual Medicine, vol. 1, 2013.

Harder, et al.: "RNase 7, a Novel Innate Immune Defense Antimicrobial Protein of Healthy Human Skin", The Journal of Biological Chemistry, vol. 277, Nov. 29, 2002.

Hearps, et al.: "Vaginal lactic acid elicits an anti inflammatory response from human cervicovaginal epithelial cells and inhibits production of pro-inflammatory mediators associated with HIV acquisition", www.nature.com/mi, vol. 10, Nov. 2017.

Hummelen, et al.: "Vaginal Microbiome and Epithelial Gene Array in Post-Menopausal Women with Moderate to Severe Dryness", Plos One, vol. 6, Nov. 2011.

Ibanez, et al.: "Pharmacological Induction of Heme Oxygenase-1 Impairs Nuclear Accumulation of Herpes Simplex Virus Capsids upon Infection", Frontiers in Microbiology, vol. 8, Oct. 2017.

Idoji, et al.: "In silico study of whey-acidic-protein domain containing oral protease inhibitors", International Journal of Molecular Medicine, vol. 21, 2008.

Jelinsky, et al.: "Molecular analysis of the vaginal response to estrogens in the ovariectomized rat and postmenopausal woman", BMC Medical Genomics, vol. I, Jun. 25, 2008.

Joly, et al.: "Nlrp10 is essential for protective anti-fungal adaptive immunity against Candida albicans", J Immunol., vol. 189, Nov. 15, 2012.

Kagan, et al.: "Restoring vaginal function in postmenopausal women with genitourinary syndrome of menopause", Menopause, vol. 25, 2018.

Kallak, et al.: "Vaginal Gene Expression During Treatment With Aromatase Inhibitors", Clinical Breast Cancer, vol. 15, Jul. 6, 2015.

Karaman, et al.: "Vascular endothelial growth factor signaling in development and disease", The Company of Biologists Ltd, vol. 145, 2018.

Kemmeren, et al.: "Risk of Arterial Thrombosis in Relation to Oral Contraceptives (Ratio) Study Oral Contraceptives and the Risk of Ischemic Stroke", www.strokeaha.org, 2002.

Kim, et al.: "Skin Protective Effect of Epigallocatechin Gallate", International Journal of Molecular Sciences, vol. 19, Jan. 6, 2018.

Klein, et al.: "Circulating Endocannabinoid Concentrations and Sexual Arousal in Women", J Sex Med, vol. 9, Jun. 2012.

Kong, et al.: "Molecular Cloning and Expression of Keratinocyte Proline-rich Protein, a Novel Squamous Epithelial Marker Isolated During Skin Development", The Journal of Biological Chemistry, vol. 278, Jun. 20, 2003.

Liu' et al.: "Olfactomedin 4 down-regulates innate immunity against Helicobacter pylori infection", PNAS, vol. 107, Jun. 15, 2010.

Marshall, et al.: "Differentially expressed late constituents of the epidermal cornified envelope", PNAS, vol. 98, Nov. 6, 2001.

McGrath, et al.: "The filaggrin story: novel insights into skin-barrier function and disease", Trends Mol Med., vol. 14, Jan. 2008.

Mirmonsef, et al.: "Free Glycogen in Vaginal Fluids Is Associated with Lactobacillus Colonization and Low Vaginal pH", Plos One, vol. 9, Jul. 2014.

Mitchell, et al.: "Vaginal microbiota and genitourinary menopausal symptoms: A cross sectional analysis", Menopause, vol. 24, Oct. 2017.

Mitchell, et al.: "Associations between improvement in genitourinary symptoms of menopause and changes in the vaginal ecosystem", Menopause, vol. 25, 2017.

Muller, et al.: "Cannabinoid Ligands Targeting TRP Channels", Frontiers in Molecular Neuroscience, vol. 11, Jan. 15, 2019.

Naumova, et al.: "Current treatment options for postmenopausal vaginal atrophy", International Journal of Women's Health, vol. 10, 2018.

Niehaus, et al.: "Human Serpinb 12 Is an Abundant Intracellular Serpin Expressed in Most Surface and Glandular Epithelia", Journal of Histochemistry & Cytochemistry, vol. 63, Jul. 15, 2015.

Park, et al.: "Suprabasin, a Novel Epidermal Differentiation Marker and Potential Cornified Envelope Precursor", J Biol Chem., vol. 277, Nov. 22, 2002.

Pinkerton, et al.: "The 2017 hormone therapy position statement of The North American Menopause Society", Menopause: The Journal of the North American Menopause Society, vol. 24, Apr. 6, 2017.

Rajeevan, et al.: "Pathway-focused genetic evaluation of immune and inflammation related genes with chronic fatigue syndrome", Human Immunology, vol. 75, Jun. 14, 2015.

Riethmuller, et al.: "Filaggrin breakdown products determine corneocyte conformation in patients with atopic dermatitis", American Academy of Allergy, Asthma & Immunology, vol. 136, Apr. 24, 2015.

Santoro, et al.: "Prevalence and Impact of Vaginal Symptoms among Postmenopausal Women", J Sex Med, vol. 6, 2009.

Shumaker, et al.: "Conjugated Equine Estrogens and Incidence of Probable Dementia and Mild Cognitive Impairment in Postmenopausal Women", JAMA, vol. 291, Jun. 23/30, 2004.

Solomon, et al.: "Effect of Delta-9-Tetrahydrocannabinol on Uterine and Vaginal Cytology of Ovariectomized Rat", Science, New Series, vol. 195, Mar. 4, 1977.

Stachenfeld, et al.: "Hormonal Changes During Menopause and the Impact on Fluid Regulation", Reproductive Sciences, vol. 21, 2014.

Steinhoff, et al.: "A TR(I)P to Pruritus Research: Role of TRPV3 in Inflammation and Itch", Journal of Investigative Dermatology, vol. 129, 2009.

Sturniolo, et al.: "A Novel Tumor Suppressor Protein Promotes Keratinocyte Terminal Differentiation via Activation of Type I Transglutaminase", The Journal of Biological Chemistry, vol. 278, Nov. 28, 2003.

Song, et al.: "Choline transporter-like protein 4 (CTL4) links to non-neuronal acetylcholine synthesis", J Neurochem, vol. 126, Aug. 2013.

Ting, et al.: "Estrogen Regulates Vaginal Sensory and Autonomic Nerve Density in the Rat", Biology of Reproduction, vol. 71.

Tóth, et al.: "Cannabinoid Signaling in the Skin: Therapeutic Potential of the "C(ut)annabinoid" System", Molecules, vol. 24, Mar. 6, 2019.

(56) References Cited

OTHER PUBLICATIONS

Toulza, t al.: "Large-scale identification of human genes implicated in epidermal barrier function", Genome Biology, vol. 8, Jun. 11, 2007.
Walker, et al.: "The role of the endocannabinoid system in (11)c" female reproductive tissues", Journal of Ovarian Research, vol. 12, 2019.
Xi, et al.: "Role of novel type I interferon epsilon in viral infection and mucosal immunity", www.nature.com/mi, vol. 5, Nov. 2012.
E Yamamoto-Kasai et al.: "TRPV3 as a Therapeutic Target for Itch", Journal of Investigative Dermatology, vol. 132, Apr. 5, 2012.
Wu, et al.: "Molecular Identification and Expression Analysis of Filaggrin-2, a Member of the 5100 Fused-Type Protein Family", Plos One, vol. 4, Apr. 2009.
Y Sato et al.: "Ascorbic Acid Deficiency Leads to Epidermal Atrophy and UVB-Induced Skin Pigmentation in SMP30/GNL Knockout Hairless Mice", Journal of Investigative Dermatology, vol. 132, Apr. 12, 2012.
Zhang, et al.: "A9-tetrahydrocannabinol inhibits epithelial-mesenchymal transition and metastasis by targeting matrix metalloproteinase-9 in endometrial cancer", Oncology Letters, vol. 15, Feb. 28, 2018.
Zhu, et al.: "Age at natural menopause and risk of incident cardiovascular disease: a pooled analysis of individual patient data", www.thelancet.com/public-health, Oct. 3, 2019.

\* cited by examiner

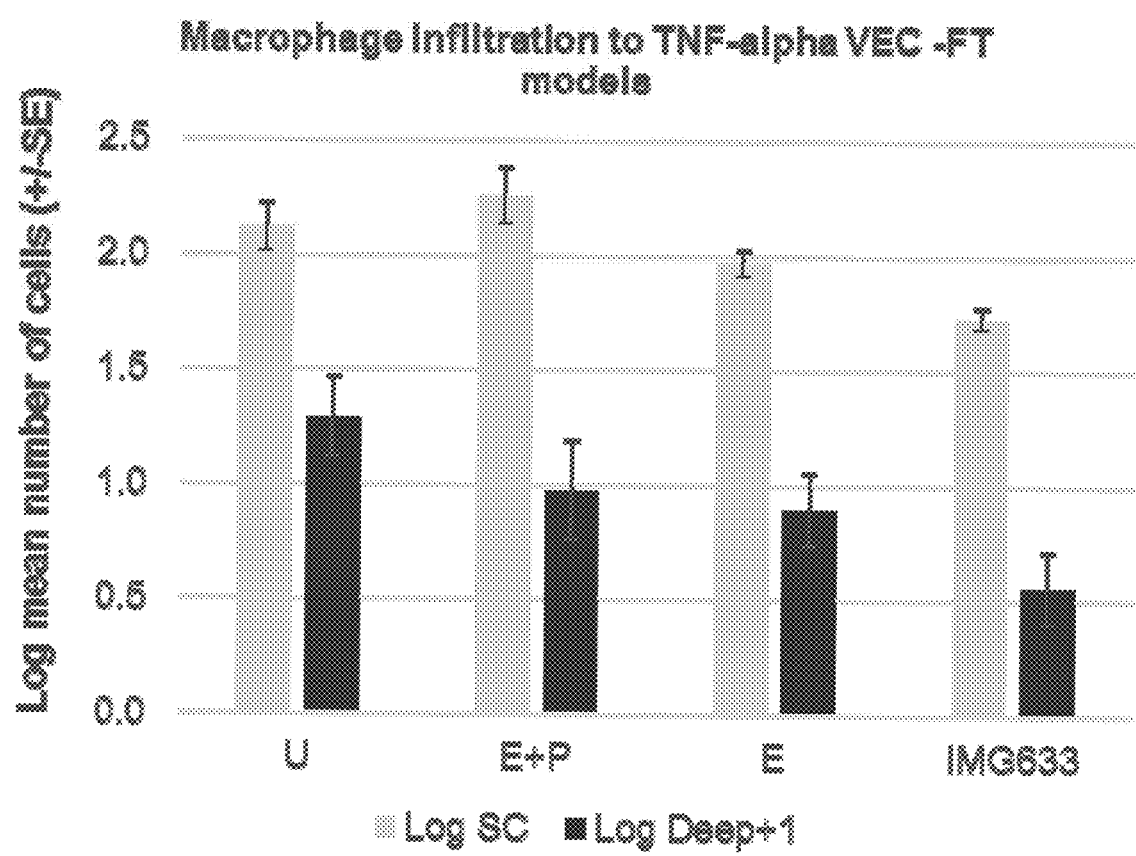

NON-HORMONAL TREATMENT OF THE GENITOURINARY SYNDROME OF MENOPAUSE

CROSS-REFERENCE TO RELATED APPLICATION

This application claims priority to U.S. Provisional Application No. 62/627,430 filed Feb. 7, 2018, which is herein incorporated by reference in its entirety.

FIELD OF THE INVENTION

The invention relates generally to the fields of pharmacology and medicine. In particular, the invention relates to compounds for treating the genitourinary syndrome of menopause (GSM) in an individual in need thereof.

BACKGROUND

Menopause is a condition that naturally affects all women who live beyond the age of 45 or women who undergo complete hysterectomy with the removal of their ovaries or are required to take an aromatase inhibitor due to estrogen receptor-sensitive breast cancer. The result of menopause is the cessation of menstrual periods and the loss of reproduction due to the attrition and eventual failure of oocytes to produce estrogen and progesterone which are needed for the implantation and support of an embryo. Menopause usually ends by the age of 51 in the West but can occur earlier in the Philippines and in India. The loss of the reproductive hormones and the continued production of the follicle stimulating and luteinizing hormones produced by the pituitary gland which are responsible for the menstrual cycle lead to a variety of symptoms and conditions associated with menopause such as hot flashes, osteopenia, mood swings, insomnia, and vulvar and vaginal atrophy (VVA) which may or may not be due to this dysregulation.

Unlike vasomotor symptoms which improve over time, the genitourinary syndrome of menopause (GSM) is a chronic and progressive condition and will not resolve without therapeutic intervention. Almost 50% of women who go through menopause experience recurrent urinary tract infections (RUTI), and VVA which is associated with dryness, irritation, itching, and dyspareunia. As the vaginal introitus retracts, the urethral meatus is more exposed and subject to infection. The effects that these symptoms have on menopausal women can be devastating from a psychosocial standpoint—loss of self-esteem based on sexual dysfunction as well as the odors associated with incontinence in addition to the sleep loss caused by nocturia which can affect mood, interpersonal relationships and the quality of life (QOL). The pain and discomfort of the sexual encounter can contribute to the stress of a conjugal relationship and even threaten its existence. The decreased thickness of the vaginal wall, loss of elasticity, drying and increasing pH can all contribute to microabrasions and increase the risk of sexually transmitted diseases including Human Immunodeficiency Virus (HIV).

Menopausal hormone replacement therapy (MHT) or hormone replacement therapy (HRT) has been the mainstay of therapy for more than fifty years. In a 2017 position statement by the North American Menopause Society, hormone therapy remains the most effective treatment for vasomotor symptoms (VMS) and GSM but also has been shown to prevent bone loss and fracture. Not only does it treat the VMS, e.g., hot flashes and night sweats, it also treats the vaginal symptoms of dryness, irritation, itching and dyspareunia which are the result of thinning of the vaginal epithelium. Another factor affected by the loss of 17β-estradiol is the loss of elasticity of vulvovaginal tissues.

Additionally it has been shown in ovarectomized rats that the density of autonomic nerve endings increases, particularly sympathetic nerve endings which lead to vasoconstriction and dryness as well as an increase in sensory nociceptor nerves which result in pain, burning and itching. The systemic administration of estrogen reduces nerve density comparable to normal cycling rats. However, the effects of estrogen go beyond increasing the thickness of the vaginal epithelium and the reduction of nerve endings; it regulates the growth and function of vascular and nonvascular smooth muscle which improves vaginal wall perfusion and vaginal wall smooth muscle tone. However, the benefits of MHT are dependent on the initiation of the treatment—women younger than 60 or who start within 10 years of the onset of menopause have the most favorable results compared to women aged 60 years or older who have an increased risk of coronary heart disease, stroke, venous thromboembolism and dementia. However, a recent analysis of long-term all-cause mortality of women showed that there was virtually no risk associated with taking MHT.

Regardless of the facts regarding the risks of MHT, less then 25% of menopausal women in the Western world take MHT for the treatment of their symptoms. In a 2008 internet survey, past and never MHT users have a 48% and 51%, respectively, overall concern about the safety of the hormones. In the group that never used MHT, they stated that up to 94% of their physicians had not suggested taking MHT for VMS, VVA or other reasons. Their concern for safety was more related to reading magazines, followed by television and newspapers. The reason given by 26% of those who never took MHT was because they felt that their symptoms would go away over time. The amount of relief provided by over-the-counter lubricants or mositurizers was reported to be quite low and that their use was bothersome. The relief provided by the selective estrogen receptor modulator (SERM) ospemifene has been significant as measured by the vaginal maturation index, decreasing pH, reduction in dryness and dyspareunia and not associated with endometrial or breast-safety concerns; however, its use has not been widely embraced due to cost and side effects. Effective treatments for the GSM that are convenient to use and that lack undesirable side effects are greatly needed.

SUMMARY

Described herein are methods of administering compounds capable of modulating expression of genes involved in the GSM for treating the GSM in an individual. Compounds L759,633 and JWH-133, which are selective ligands for the endocannabinoid receptor type 2 (CB2), can be used as a non-hormonal alternative to estrogen and ospemiphene for the treatment of the GSM and in particular, VVA.

Accordingly, described herein is a method of treating genitourinary syndrome of menopause in an individual. The method includes administering to the individual a composition including a pharmaceutically acceptable carrier and a therapeutically effective amount of:

i) a compound having the formula:

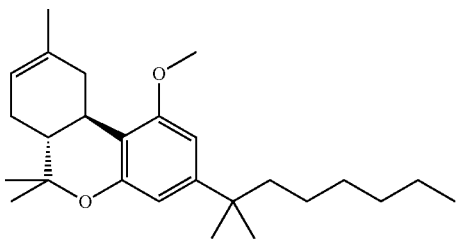 [SMILES: CCCCCCC(C)(C)c1cc(OC)c2c(c1)OC(C)(C)[C@@H]1CC=C(C)C[C@@H]21]

or
ii) a compound having the formula:

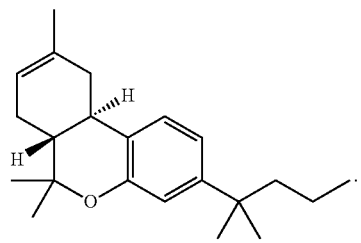 [SMILES: CCCC(C)(C)c1ccc2c(c1)OC(C)(C)[C@@H]1CC=C(C)C[C@@H]21]

In the method, the individual typically is a human female. In the method the genitourinary syndrome of menopause includes at least one of: vulvovaginal atrophy, vaginal dryness, prurutis, incontinence, dyspareunia, and recurrent urinary tract infections, and administration of the composition ameliorates at least one of: vulvovaginal atrophy, vaginal dryness, incontinence, dyspareunia, and recurrent urinary tract infections in the individual. The individual can have vulvovaginal atrophy resulting from, for example, loss of estrogen during perimenopause and/or menopause, from surgical removal of ovaries, from use of aromatase inhibitors during treatment of breast cancer, etc. In the method, the therapeutically effective amount is an amount sufficient to, for example, increase mucin production in the individual's vagina, increase keratin fiber synthesis and keratin fiber cross-linking in the individual's vagina, decrease cytokine, chemokine and matrix metalloproteinas expression in the individual's vagina, increase vascularization and blood flow in the individual's vagina, etc. In some embodiments of the method, the composition further includes an estrogen steroid hormone.

Also described herein is a method of modulating an individual's vaginal microbiome. The method includes administering to the individual a composition including a pharmaceutically acceptable carrier and a therapeutically effective amount of:
i) a compound having the formula:

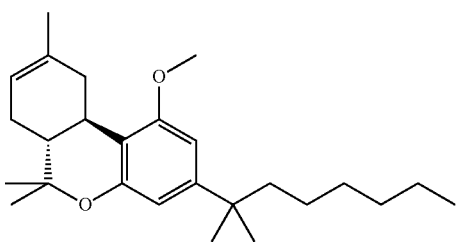 [SMILES: CCCCCCC(C)(C)c1cc(OC)c2c(c1)OC(C)(C)[C@@H]1CC=C(C)C[C@@H]21]

or
ii) a compound having the formula:

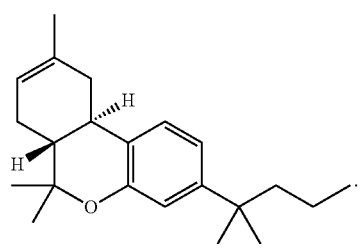 [SMILES: CCCC(C)(C)c1ccc2c(c1)OC(C)(C)[C@@H]1CC=C(C)C[C@@H]21]

In the method, the individual typically is a human female. In the method, the therapeutically effective amount is an amount effective for at least one of: increasing glycogen production for promoting *Lactobacillus* colonization and decreasing pH in the individual's vagina, increasing RNAase7 expression for anti-bacterial activity, and increasing NLRP10 expression for anti-fungal activity. The individual can have at least one of: vulvovaginal atrophy, vaginal dryness, incontinence, dyspareunia, and recurrent urinary tract infections. In some embodiments, the individual has two or more of these conditions (two or more of vulvovaginal atrophy, vaginal dryness, incontinence, dyspareunia, and recurrent urinary tract infections). The individual can have vulvovaginal atrophy resulting from, for example, loss of estrogen during perimenopause and/or menopause, surgical removal of ovaries, use of aromatase inhibitors during and after treatment of breast cancer, etc.

Further described herein is a method of increasing or decreasing expression of any one gene from any one or more of Tables 1-9 in an individual. The method includes administering to the individual a composition including a pharmaceutically acceptable carrier and an amount of:
i) a compound having the formula:

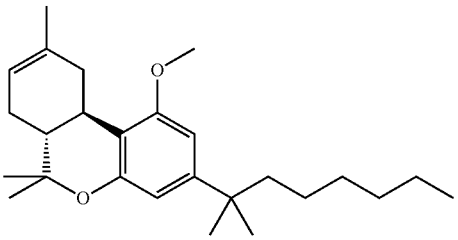 [SMILES: CCCCCCC(C)(C)c1cc(OC)c2c(c1)OC(C)(C)[C@@H]1CC=C(C)C[C@@H]21]

or
ii) a compound having the formula:

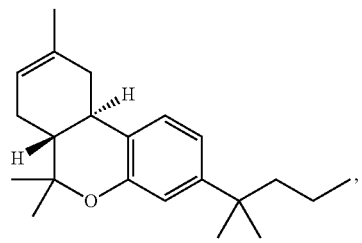

the amount therapeutically effective for increasing or decreasing expression of any one gene from any one or more of Tables 1-9. Increasing or decreasing expression of one or more genes from Table 3 can increase growth and/or differentiation of cells of the vaginal epithelium in the individual's vagina. Increasing expression of one or more genes of Table 1 typically results in inhibition of growth and/or activity of at least one of: pathogenic bacteria, yeast and viruses. Increasing expression of one or more genes of Table 2 typically results in increasing moisture content of the vaginal epithelium in the individual's vagina. Increasing expression of one or more genes of Table 4 typically improves barrier function in the individual's vaginal epithelium. Increasing expression of gene VEGFA and gene TRPV3 typically increases vascularity and blood flow in the individual's vagina. Increasing expression of the TPRV3 gene can increase expression of the vanilloid receptor. In the method, expression one or more (e.g., 1, 2, 3, 4, 5, 10, etc.) genes from Table 1 can be modulated (increased or decreased) by administering compound L759,633 or compound JWH-133. In the method, expression one or more (e.g., 1, 2, 3, 4, 5, 10, etc.) genes from Table 2 can be modulated (increased or decreased) by administering compound L759,633 or compound JWH-133. In the method, expression one or more (e.g., 1, 2, 3, 4, 5, 10, etc.) genes from Table 3 can be modulated by administering compound L759,633 or compound JWH-133. In the method, expression one or more (e.g., 1, 2, 3, 4, 5, 10, etc.) genes from Table 4 can be modulated by administering compound L759,633 or compound JWH-133. In the method, expression one or more (e.g., 1, 2, 3, 4, 5, 10, etc.) genes from Table 5 can be modulated by administering compound L759,633 or compound JWH-133. In the method, expression one or more (e.g., 1, 2, 3, 4, 5, 10, etc.) genes from Table 6 can be modulated by administering compound L759,633 or compound JWH-133. In the method, expression one or more (e.g., 1, 2, 3, 4, 5, 10, etc.) genes from Table 7 can be modulated by administering compound L759,633 or compound JWH-133. In the method, expression one or more (e.g., 1, 2, 3, 4, 5, 10, etc.) genes from Table 8 can be modulated by administering compound L759,633 or compound JWH-133. In the method, expression one or more (e.g., 1, 2, 3, 4, 5, 10, etc.) genes from Table 9 can be modulated by administering compound L759,633 or compound JWH-133. In some embodiments, expression of genes from multiple tables is modulated. For example, expression of at least one gene from Table 1 and at least one gene from Table 5 can be modulated. In another example, expression of at least one gene from Table 2 and at least one gene from Table 7 can be modulated. In another example, expression of at least one gene from Table 1, at least one gene from Table 2, at least one gene from Table 3, at least one gene from Table 4, at least one gene from Table 5, at least one gene from Table 6, at least one gene from Table 7, at least one gene from Table 8, and at least one gene from Table 9 can be modulated (i.e., expression of at least one gene from every table of Tables 1-9 can be modulated).

By the terms "Compound L759,633" and "L759,633" is meant a compound of the formula:

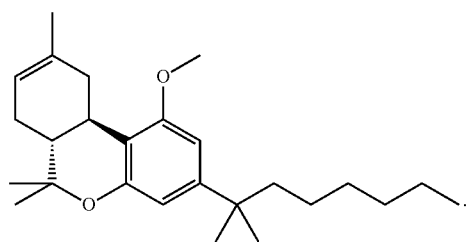 [SMILES: CCCCCCC(C)(C)c1cc(OC)c2c(c1)OC(C)(C)[C@@H]1CC=C(C)C[C@@H]21]

L759,633 is a partial agonist as determined by its inhibitory effects on receptor internationalization.

As used herein, the terms "Compound JWH-133" and "JWH-133" mean a compound having the formula:

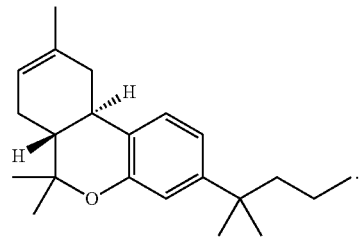 [SMILES: CCCC(C)(C)c1ccc2c(c1)OC(C)(C)[C@@H]1CC=C(C)C[C@@H]21]

JWH-133 is a full agonist by the same criterion of receptor internalization and its promotion of receptor internalization As used herein, the term "antimicrobial" applies to an agent which is used to treat an infection either through its elimination or reduction in growth or limitation of its pathogenicity or invasiveness This applies to bacteria, yeast, viruses and protozoa.

By the term "up-regulated" when referring to expression of a gene means 1.5 fold or greater increased expression relative to normal expression.

As used herein, the term "down-regulated" when referring to expression of a gene means—1.5 fold or greater decreased expression relative to normal expression.

The term "purified" means separated from many other entities (small molecules, compounds, proteins, nucleic acids), and does not require the material to be present in a form exhibiting absolute purity, exclusive of the presence of other entities. In some embodiments, a compound, small molecule, protein, nucleic acid or other entity is considered pure (purified) when it is removed from substantially all other entities.

By the terms "to modulate" and "modulates" is meant to increase or decrease. These terms can refer to increasing or decreasing an activity, level or function of a molecule (e.g., protein, peptide, nucleic acid, small molecule, metabolite), or effecting a change with respect to one or more biological or physiological mechanisms, effects, responses, functions, pathways or activities in which, for example, VVA is involved.

The terms "agent" and "therapeutic agent" as used herein refer to a chemical entity or biological product, or combination of chemical entities or biological products, administered to a subject (a mammal such as a human) to treat a disease or condition (e.g., the GSM). Examples of therapeutic agents include small molecules (compounds) and biologics, which may be referred to herein as a "drug" or "therapeutic drug". Compounds L759,633 and JWH-133 are therapeutic agents (therapeutic drugs).

The terms "patient," "subject" and "individual" are used interchangeably herein, and mean a subject, typically a mammal, to be treated, diagnosed, and/or to obtain a biological sample from. Subjects include, but are not limited to, humans, non-human primates, horses, cows, sheep, pigs, rats, mice, insects, dogs, and cats. A human female in need of treatment for the GSM is an example of a subject.

The terms "sample," "patient sample," "biological sample," and the like, encompass a variety of sample types obtained from a patient, individual, or subject and can be used in a therapeutic drug screening, diagnostic or monitoring assay. The patient sample may be obtained from a healthy subject, a diseased patient or a patient having associated symptoms of a particular disease or disorder (e.g., the GSM). The definition specifically encompasses blood and other liquid samples of biological origin (including, e.g., vaginal fluid, plasma, serum, peripheral blood), solid tissue samples such as a biopsy specimen or tissue cultures or cells derived therefrom and the progeny thereof. The terms encompass a clinical sample, and also include cells in culture, cell supernatants, tissue samples, and the like. Samples may also comprise fresh-frozen and/or formalin-fixed, paraffin-embedded tissue blocks, such as blocks prepared from clinical or pathological biopsies, prepared for pathological analysis or study by immunohistochemistry.

As used herein, the terms "therapeutic treatment" and "therapy" are defined as the application or administration of a therapeutic agent (e.g., compound L759,633, compound JWH-133) or therapeutic agents to a patient who has a disease, a symptom of disease or a predisposition toward a disease, with the purpose to cure, heal, alleviate, relieve, alter, remedy, ameliorate, improve or affect the disease, the symptoms of disease, or the predisposition toward disease.

Although compounds, compositions, methods and kits similar or equivalent to those described herein can be used in the practice or testing of the present invention, suitable compounds, compositions, methods and kits are described below. All publications, patent applications, and patents mentioned herein are incorporated by reference in their entirety. In the case of conflict, the present specification, including definitions, will control. The particular embodiments discussed below are illustrative only and not intended to be limiting.

BRIEF DESCRIPTION OF THE DRAWINGS

FIG. 1 is a graph showing macrophage infiltration in hormone (estrogen) and L759,633-treated EpiVaginal tissues. L759,633 had the most striking effect on macrophage infiltration: only 6% of cells infiltrated into the tissue past 90 μm (vs. 28% into the untreated tissue, p<0.006 ANOVA). The estrogen treatment showed a similar effect, but not as dramatic (16% vs 28%, not significant due to high variability). U=untreated control; E=estradiol; P=progesterone; and IMG=the cannabinoid L759,633.

DETAILED DESCRIPTION

Described herein are novel methods of alleviating or treating the GSM in an individual (e.g., human female having the GSM). The methods include administering compound L759,633 or compound JWH-133 to an individual having the GSM. In the methods, administration of compound L759,633 or compound JWH-133 results in modulation of expression of genes involved in or associated with vaginal health and vaginal function (e.g., genes listed in Tables 1-9). In a typical embodiment, an effective amount of compound L759,633 or compound JWH-133 is administered to an individual in the absence of any hormones (e.g., estradiol), but in some embodiments, compound L759,633 or compound JWH-133 may be administered in combination with a hormone (e.g., estradiol for treatment of vasomotor symptoms). In the Examples below, compound L759,633 and compound JWH-133 were shown to modulate expression of genes (see Tables 1-9) associated with vaginal dryness, desquamation, vaginal tissue repair, vaginal blood flow, the vaginal microbiome, and pathogen defense, i.e. antimicrobial function and innate and adaptive immune responses.

Compound L759,633 and Compound JWH-133

Methods of treating the GSM in an individual include administering to the individual (e.g., human female) a composition including a pharmaceutically acceptable carrier and a therapeutically effective amount of compound L759,633 or compound JWH-133. Methods of synthesizing compounds L759,633 and JWH-133 are known in the art. Compounds L759,633 and JWH-133 may be synthesized or prepared according to any suitable method, or may be commercially obtained (e.g., Tocris Biosciences: JWH-133 Cat. No. 1343/10; L759,633 Cat. No. 2433/10).

These compounds may be formulated with any pharmaceutically acceptable carrier according to conventional pharmaceutical practice (see, e.g., Remington: The Science and Practice of Pharmacy (21st ed.), ed. A. R. Gennaro, Lippincott Williams & Wilkins, (2005) and Encyclopedia of Pharmaceutical Technology, ($3^{rd}$ ed.) eds. J. Swarbrick and J. C. Boylan, Marcel Dekker, CRC Press, New York (2006), a standard text in this field, and in USP/NF). A description of exemplary pharmaceutically acceptable carriers, excipients and diluents, as well as pharmaceutical formulations, can be found in Remington: supra. Other substances may be added to the compounds and compositions to stabilize and/or preserve them.

In some embodiments, compound L759,633 or compound JWH-133 is combined with an estrogen steroid hormone (e.g., estradiol and other estrogens) which would be beneficial for alleviating the VMS (e.g., hot flashes, night sweats and flushes) in an individual suffering from the GSM. In such embodiments, any suitable estrogen or estrogen-like steroid hormone can be used. In addition to estradiol, examples of estrogens include conjugated estrogens, estradiol derivatives, estrone derivatives, estriol derivatives and their epimers, etc.

Methods of Treating the GSM in an Individual

Methods of treating the GSM in an individual (e.g., human female) include administering to the individual a composition including a pharmaceutically acceptable carrier and a therapeutically effective amount of compound L759,633 or compound JWH-133. Compounds L759,633 and JWH-133 and compositions containing these compounds may be used to treat, reduce or prevent any condition associated with or caused by the GSM. Specific examples of conditions associated with or caused by the GSM include VVA, RUTI, dyspareunia, vaginal dryness, vaginal irritation (e.g., pain), vaginal itching, incontinence, loss of vulvovaginal tissue elasticity, loss of vaginal wall thickness, increased vaginal pH, increased risk of sexually transmitted disease, and decreased immune function. In some embodiments, the individual having the GSM is suffering from VVA.

If the individual has VVA, the VVA can be caused by or result from any procedure or condition. For example, in some embodiments, the VVA can result from loss of estrogen during perimenopause and/or menopause. In other embodiments, the individual has VVA resulting from surgical removal of ovaries, or from use of aromatase inhibitors during treatment of breast cancer.

In the methods, typically an effective amount of compound L759,633 or compound JWH-133 is an amount sufficient to result in one or more of the following: increased mucin production in the individual's vagina; increased moisture in the individual's vagina; increased growth and/or differentiation of cells (e.g., keratinocytes) in the vaginal epithelium of the individual; increased keratin fiber synthesis and keratin fiber cross-linking in the individual's vagina; decreased cytokine, chemokine and matrix metalloproteinase expression in the individual's vagina; increased vascularization (angiogenesis) and blood flow in the individual's vagina; decreased undesirable bacterial, fungal and viral growth in the individual's vagina; improved barrier function in the individual's vaginal epithelium; and improvement of the vaginal microbiome (e.g., increase desirable microbial growth in the vagina).

In a method of modulating (improving) the microbiome of an individual's vagina, a composition including a pharmaceutically acceptable carrier and a therapeutically effective amount of compound L759,633 or compound JWH-133 is administered to the individual. In a typical method, the therapeutically effective amount is an amount effective for at least one of: increasing GYS2(liver) gene expression responsible for glycogen production for promoting *Lactobacillus* colonization and decreasing pH in the individual's vagina, increasing RNAase7 expression for anti-bacterial activity, increasing NLRP10 expression for anti-fungal activity, increasing Interferon epsilon (IFNE) expression for antiviral activity, increasing expression levels and/or activity of kallikrein-peptidases which release anti-microbial peptides (AMP), increasing the gene expression of whey acidic proteins (WFDC) 5 and 12 which have antimicrobial and antiprotease activity (Idoii et al., Int J Mol Med, vol. 21, no. 4, pp. 461-468), and increasing SERPINB12 expression and/or activity which inhibits exogenous viral and bacterial proteases or protects from endogenous proteases involved with immune defense. See Table 1 below for genes associated with antimicrobial activity that are differentially expressed (upregulated or downregulated) due to exposure to compound L759,633 or compound JWH-133. In this table, all genes are upregulated by compound L759,633 and compound JWH-133. Specifically, up-regulation of the genes of Table 1 by JWH-133 or L759,633 can decrease undesirable bacterial, fungal and viral growth (e.g., by promoting or inducing a response against the undesirable bacteria, virus or fungus). Accordingly, in a method of modulating (improving) the microbiome of an individual's vagina, compound L759,633 or compound JWH-133 can be administered in an amount effective for increasing expression of one or more (e.g., 1, 2, 3, 4, 5, 10, etc.) genes of Table 1. In all of the tables herein, a fold-change numerical value indicates a fold-increase, whereas a fold-change numerical value that is preceded by a "–" indicates a fold-decrease.

TABLE 1

Antimicrobial Activity - a comparison of the differential gene expression induced by all three compounds (estradiol, L759,633 and JWH-133)
Genes with antimicrobial activity

| Symbol Symbol | Entrez Gene Name | Estradiol | | L759,633 | | JWH-133 | |
|---|---|---|---|---|---|---|---|
| | | Fold Change | FDR | Fold Change | FDR | Fold Change | FDR |
| KLK13 | kallikrein related peptidase 13 | 4.626 | 1.03E−05 | 3.957 | 0.0000117 | 3.278 | 0.0000279 |
| NLRP10 | NLR family pyrin domain containing 10 | 4.199 | 0.0053 | 15.93 | 0.0000397 | 10.11 | 0.00011 |
| KLK12 | kallikrein related peptidase 12 | 4.018 | 2.62E−07 | 3.933 | 0.000000987 | 3.882 | 0.00000111 |
| RNAse7 | RNAse family | 3.387 | 3.02E−06 | 8.158 | 0.0000102 | 6.145 | 0.0000221 |
| WFDC12 | WAP four-disulfide core domain 13 | 3.103 | 0.0023 | 7.884 | 0.0000226 | 5.534 | 0.0000697 |
| KLK6 | kallikrein related peptidase 6 | 2.769 | 0.001 | 4.651 | 0.0000266 | 4.063 | 0.0000512 |
| IFNE | Interferon Epsilon | 2.1 | 0.021 | 5.496 | 0.0014 | 4.439 | 0.0033 |
| KLK10 | kallikrein related peptidase 10 | 2.043 | 0.0003 | 2.554 | 0.0000191 | 2.214 | 0.0000551 |
| KLK8 | kallikrein related peptidase 8 | 1.831 | 0.0009 | 1.842 | 0.0002 | 1.504 | 0.003 |
| WFDC5 | WAP four-disulfide core domain 5 | 1.2 | 0.046 | 3.139 | 0.0002 | 2.807 | 0.0004 |
| SERPINB12 | serpin family B member 12 | 1.3 | 0.041 | 5.202 | 0.0001 | 4.409 | 0.0003 |

In some methods of treating the GSM or improving the vaginal microbiome, the individual has at least one of: VVA (e.g., VVA resulting from surgical removal of ovaries, from loss of estrogen during perimenopause and/or menopause, from use of aromatase inhibitors), vaginal dryness, incontinence, dyspareunia, and RUTI. In some embodiments, the individual has two or more of these conditions.

As described in more detail in the Examples below, methods of treating the GSM in an individual (e.g., human female) involve modulating expression of one or more (e.g., 1, 2, 3, 4, 5, 10, etc.) genes involved in vaginal health and vaginal function by administering compound L759,633 or compound JWH-133. Accordingly, a method of modulating (increasing or decreasing) expression of (i.e., upregulating or downregulating) any one (e.g., 1, 2, 5, 10, 15, 20, etc.) gene(s) from any one or more of Tables 1-9 includes administering to the individual a composition including a pharmaceutically acceptable carrier and an amount of compound L759,633 or compound JWH-133 effective for upregulating or downregulating one or more genes from any one or more of Tables 1-9. In the method, a composition including either compound (e.g., in a pharmaceutically acceptable carrier) can be administered. The therapeutically effective amount is typically an amount also sufficient to result in one or more of the following: increased moisture in the individual's vaginal epithelium; increased mucin production in the individual's vagina; increased growth and/or differentiation of cells (e.g., keratinocytes) in the vaginal epithelium; increased keratin fiber synthesis, keratin fiber cross-linking in the epithelial cells and the increased expression of cadherins and desmosomes binding the cells together in the individual's vagina; decreased cytokine, chemokine and matrix metalloproteinase expression in the individual's vagina; increased vascularization (angiogenesis) and blood flow in the individual's vagina; decreased undesirable bacterial, fungal and viral growth in the individual's vagina; improving barrier function in the individual's vaginal epithelium; and improvement of the vaginal microbiome (e.g., increase desirable microbial growth in the vagina). For example, the mucin like gene 1 (MUCL1) gene is involved in mucin production in the vagina which is up-regulated by estradiol and L759,633 (See Table 2 below). By increasing mucin production, vaginal moisture is increased. In Table 2, all genes are upregulated by JWH-133 and L759,633 except MUCL1 by JWH-133. Accordingly, in a method of treating the GSM and a method of modulating an individual's microbiome, JWH-133 and L759,633 can be administered in an amount effective for increasing expression of one or more genes of Table 2 and increasing mucin production and moisture in the individual's vagina.

TABLE 2

Genes Known to be Specifically Expressed Relating to Moisture, Vascularization, Blood Flow and Pruritis

| Symbol | Entrez Gene Name | Estradiol | | L759,633 | | JWH-133 | |
| --- | --- | --- | --- | --- | --- | --- | --- |
| | | Fold Change | FDR | Fold Change | FDR | Fold Change | FDR |
| FLG | filaggrin | 3.212 | 0.0078 | 4.549 | 0.0007 | 3.151 | 0.0039 |
| FLG2 | filaggrin family member 2 | 2.766 | 0.0238 | 10.449 | 0.0000882 | 6.801 | 0.0004 |
| MUCL1 | mucin like 1 | 2.857 | 3.41E−06 | 1.964 | 0.0022 | 1.4 | 5.90E−02 |
| TRPV3 | transient receptor potential cation channel subfamily V member 3 | 1.6 | 0.120016 | 2.804 | 0.0003 | 2.382 | 0.0009 |
| TGM1 | Transglutaminase 1 | 1.406 | 0.0906 | 1.966 | 0.0028 | 1.809 | 0.0063 |
| VEGFA | vascular endothelial growth factor A | 1.2 | 0.217 | 1.885 | 0.0098 | 1.2 | 0.768 |
| SLC44A4 | solute carrier family 44 member 4 | −1.8 | 0.0183 | −2.76 | 0.0003 | −1.978 | 0.0042 |

Specifically, up-regulation of genes filaggrin (FLG) and filaggrin 2 (FLG2) by JWH-133 or L759,633 can increase the moisture content of the stratum corneum in the individual's vagina as a result of their degradation (Table 2). The upregulation of transglutaminase 1 by L759,633 and JWH-133 (Kim et al. International journal of molecular sciences, 2018, 19(1): 173) also provides a means of increasing the moisture content to the vaginal epithelium (Table 2). As another example, genes involved in keratin fiber synthesis and keratin fiber-crossing that are up-regulated or down-regulated by JWH-133 or L759,633 are shown in Table 3 below. In Table 3, some genes are upregulated by exposure to L759,633 and JWH-133, and some genes are downregulated by exposure to L759,633 and JWH-133. Accordingly, in a method of treating the GSM and a method of modulating an individual's microbiome, JWH-133 and L759,633 can be administered in an amount effective for increasing expression of one or more genes of Table 3 and/or decreasing expression of one or more genes of Table 3.

TABLE 3

Growth, Structure, Differentiation of Keratinocytes
Genes known to be specifically expressed in the suprabasal layers and the epidermis

| Symbol | Entrez Gene Name | Estradiol Fold Change | FDR | L759,633 Fold Change | FDR | JWH-133 Fold Change | FDR |
|---|---|---|---|---|---|---|---|
| TGM3 | Transglutaminase 3 | 15.681 | 0.00000509 | 30.074 | 0.00000152 | 23.784 | 3.49E−06 |
| KRTDAP | keratinocyte differentiation associated protein | 13.936 | 0.0000113 | 15.751 | 0.00000738 | 9.891 | 0.0000207 |
| KPRP | human keratinocyte proline rich protein | 5.557 | 0.0068 | 25.318 | 0.0000581 | 17.392 | 0.0001 |
| DSG1 | desmoglein 1 | 4.964 | 0.0002 | 9.191 | 0.0000133 | 7.572 | 0.0000271 |
| SPRR2G | small proline rich protein 2G | 4.664 | 0.0014 | 10.387 | 0.0000347 | 7.539 | 0.0000911 |
| SBSN | suprabasin | 3.449 | 0.0000483 | 4.36 | 0.0000117 | 3.488 | 0.0000285 |
| CDSN | Corneodesmosin | 3.011 | 0.0116 | 9.465 | 0.0000683 | 6.888 | 0.0002 |
| SPRR2D | small proline rich protein 2E | 2.793 | 0.0000302 | 3.431 | 0.00000812 | 2.839 | 0.0000208 |
| SPRR4 | small proline rich protein 4 | 2.669 | 0.0029 | 2.619 | 0.0011 | 2.263 | 0.0031 |
| DMKN | dermokine | 2.428 | 0.0000113 | 2.362 | 0.0000102 | 2.043 | 0.0000261 |
| LCE2A | late cornified envelope 2A | 2.026 | 0.0899 | 6.392 | 0.0005 | 4.097 | 0.0028 |
| KRT1 | keratin 1 | 1.949 | 0.195 | 10.739 | 0.0005 | 7.122 | 0.0019 |
| LCE2C/LCE2D | late cornified envelope 2D | 1.903 | 0.393 | 24.247 | 0.001 | 10.393 | 0.0066 |
| KRT23 | keratin 23 | 1.891 | | 1.912 | 0.0000338 | 1.631 | 0.0002 |
| LCE2B | late cornified envelope 2B | 1.89 | 0.229 | 11.182 | 0.0006 | 7.398 | 0.0021 |
| DSC1 | desmocollin 1 | 1.673 | 0.259 | 10.494 | 0.0003 | 6.69 | 0.0011 |
| KRT24 | keratin 24 | 1.673 | 0.0011 | 1.619 | 0.0005 | 1.699 | 0.0003 |
| LCE5A | late cornified envelope 5A | 1.454 | 0.034 | 1.63 | 0.0056 | 1.571 | 0.0086 |
| TGM1 | Transglutaminase 1 | 1.406 | 0.0906 | 1.966 | 0.0028 | 1.809 | 0.0063 |
| LCE1F | late cornified envelope 1F | 1.317 | 0.148 | 1.593 | 0.0199 | 1.576 | 0.0212 |
| LCE1A | late cornified envelope 1A | 1.307 | 0.125 | 1.884 | 0.002 | 1.526 | 0.019 |
| CNFN | cornifelin | 1.3 | 0.1163 | 1.62 | 0.0002 | 1.706 | 0.0001 |
| DSC2 | desmocollin 2 | 1.3 | 0.059 | 1.7 | 0.005 | 1.6 | 0.014 |
| LCE1C | late cornified envelope 1C | 1.262 | 0.6 | 4.063 | 0.0051 | 2.292 | 0.0598 |
| KRT2 | keratin 2 | 1.214 | 0.34 | 1.801 | 0.0097 | 1.764 | 0.0117 |
| LOR | loricrin | 1.207 | 0.65 | 7.932 | 0.0014 | 5.085 | 0.0014 |
| DCS3 | descmocollin 3 | 1.2 | 0.11 | 1.9 | 0.0043 | 1.5 | 0.0728 |
| TGM5 | Transglutaminase 5 | 1.135 | 0.386 | 2.237 | 0.0002 | 2.346 | 0.0002 |
| KRT20 | keratin 20 | −3.702 | 0.0000143 | −3.42 | 0.0000133 | −2.992 | 0.0000291 |

Genes involved with lipid metabolism which provides for the lamellar structures of the stratum corneum of the terminally differentiated keratinocyte which prevents the leakage of solutes, water and proteins thereby preventing dessication as well as strengthening the dead cell layer that provides an element of innate immune defense. Lipid metabolism genes (genes associated with lipid metabolism) are shown below in Table 4. In particular, the upregulation of PLA2GF leads to the acidification of the SC which in turn leads to the degradation of the filaggrins which provide a natural moisturizing effect. Accordingly, in a method of treating the GSM and a method of modulating an individual's microbiome, JWH-133 and L759,633 can be administered in an amount effective for modulating expression of one or more genes of Table 4.

TABLE 4

Lipid Metabolism Genes (Genes known to be specifically expressed relating to lipid metabolism in the epidermis)

| Symbol | Entrez Gene Name | Estradiol Fold Change | FDR | L759,633 Fold Change | FDR | JWH-133 Fold Change | FDR |
|---|---|---|---|---|---|---|---|
| LIPN | lipase family member N | 4.57 | 0.0025 | 7.346 | 0.0001 | 4.766 | 0.0007 |
| LIPM | lipase family member M | 3.572 | 0.0068 | 11.426 | 5.43E−05 | 6.813 | 0.0003 |
| LIPN1 | lipin 1 | 2.831 | 0.002 | 3.775 | 0.0001 | 3.23 | 0.0003 |

TABLE 4-continued

Lipid Metabolism Genes (Genes known to be specifically expressed relating to lipid metabolism in the epidermis)

| Symbol | Entrez Gene Name | Estradiol | | L759,633 | | JWH-133 | |
|---|---|---|---|---|---|---|---|
| | | Fold Change | FDR | Fold Change | FDR | Fold Change | FDR |
| PLA2G4E | phospholipase A2 group IVE | 2.442 | 0.004 | 3.36 | 0.0002 | 2.225 | 0.003 |
| ALOX12B | arachidonate 12-lipoxygenase, 12R type | 2.207 | 0.02 | 6.683 | 5.75E−05 | 6.023 | 9.34E−05 |
| PLA2G4D | phospholipase A2 group IVD | 2.046 | 0.0031 | 3.526 | 3.63E−05 | 3.604 | 4.11E−05 |
| PLA2G2F | phospholipase A2 group IIF | 1.824 | 0.0048 | 2.054 | 0.0006 | 1.564 | 0.01 |
| PLA2G3 | phospholipase A2 group III | 1.64 | 0.0019 | 2.218 | 3.38E−05 | 1.953 | 0.0001 |
| ALOXE3 | arachidonate lipoxygenase 3 | 1.371 | 0.139 | 3.659 | 8.27E−05 | 2.881 | 0.0003 |
| PLA2G10 | phospholipase A2 group X | −2.948 | 0.0005 | −3.027 | 0.0001 | −2.819 | 0.0002 |

In Table 5 genes involved in decreased cytokine, chemokine and matrix metalloproteinase expression and/or activity that are up-regulated or down-regulated by JWH-133 or L759,633 are shown. Up-regulation and down-regulation of genes listed in Table 5 by JWH-133 or L759,633 can modulate (increase, decrease) cytokine, chemokine and matrix metalloproteinase expression in the individual's vagina. Accordingly, in a method of treating the GSM and a method of modulating an individual's microbiome, JWH-133 and L759,633 can be administered in an amount effective for modulating expression of one or more genes of Table 5 and/or decreasing expression of one or more genes of Table 5. As another example and as described in the Examples below, the upregulation of the VEGFA (vascular endothelial growth factor A) gene by estradiol and L759,633 by 2.2 and 2.0 fold, respectively, leads to the proliferation and migration of endothelial cells, i.e., vascularization (angiogenesis) in the vagina of an individual suffering from VVA of menopause. Blood flow will be increased as a result of the upregulation of the TRPV3 gene which leads to the increased expression of the vallinoid receptor in the smooth muscle of blood vessels and the nerve endings which innervate them.

TABLE 5

Immune Response Genes in Common with both L759,633 and JWH-133

| Symbol | Entrez Gene Name | L759,633 | | JWH-133 | |
|---|---|---|---|---|---|
| | | Expr Fold Change(A2) | Expr False Discovery Rate (q-value)(A2) | Expr Fold Change(A1) | Expr False Discovery Rate (q-value)(A1) |
| LY6G6C | lymphocyte antigen 6 family member G6C | 6.538 | 0.0004 | 5.531 | 0.0008 |
| mir-224 | microRNA 224 | 6.266 | 0.0002 | 4.867 | 0.0005 |
| IFNE | interferon epsilon | 5.496 | 0.0014 | 4.439 | 0.0033 |
| mir-23 | microRNA 23a | 2.823 | 0.0007 | 2.983 | 0.0005 |
| IL1RL2 | interleukin 1 receptor like 2 | 2.508 | 0.0001 | 2.54 | 0.0001 |
| CXCR2 | C-X-C motif chemokine receptor 2 | 1.871 | 0.0012 | 2.121 | 0.0004 |
| NCR3LG1 | natural killer cell cytotoxicity receptor 3 ligand 1 | 2.482 | 0.0005 | 2.076 | 0.0021 |
| TIAM1 | T cell lymphoma invasion and metastasis 1 | 2.249 | 3.99E−05 | 2.018 | 0.0001 |
| NFAT5 | nuclear factor of activated T cells 5 | 2.265 | 0.0004 | 1.924 | 0.0019 |
| IL18BP | interleukin 18 binding protein | 1.532 | 0.0001 | 1.523 | 0.0002 |
| IRF9 | interferon regulatory factor 9 | −1.535 | 0.0088 | −1.62 | 0.0046 |
| UBA7 | ubiquitin like modifier activating enzyme 7 | −2.031 | 0.0002 | −1.651 | 0.0017 |
| CD151 | CD151 molecule (Raph blood group) | −1.664 | 0.0015 | −1.653 | 0.0018 |
| HLA-B | major histocompatibility complex, class I, B | −2.168 | 0.0006 | −1.677 | 0.0073 |
| CFH | complement factor H | −1.769 | 0.0005 | −1.681 | 0.001 |
| TNFAIP8 | TNF alpha induced protein 8 | −1.601 | 0.0055 | −1.724 | 0.0025 |
| PDCD1LG2 | programmed cell death 1 ligand 2 | −1.74 | 0.0011 | −1.879 | 0.0006 |
| CXCL17 | C-X-C motif chemokine ligand 17 | −2.038 | 2.32E−05 | −1.881 | 5.12E−05 |

TABLE 5-continued

Immune Response Genes in Common with both L759,633 and JWH-133

| | | L759,633 | | JWH-133 | |
|---|---|---|---|---|---|
| Symbol | Entrez Gene Name | Expr Fold Change(A2) | Expr False Discovery Rate (q-value)(A2) | Expr Fold Change(A1) | Expr False Discovery Rate (q-value)(A1) |
| CCDC59 | coiled-coil domain containing 59 | −1.795 | 0.006 | −1.956 | 0.0028 |
| IFIT5 | interferon induced protein with tetratricopeptide repeats 5 | −2.183 | 0.0002 | −1.97 | 0.0006 |
| RPS15A | ribosomal protein S15a | −1.78 | 0.0038 | −1.999 | 0.0013 |
| TNFRSF11B | TNF receptor superfamily member 11b | −2.012 | 2.11E−05 | −2.006 | 2.85E−05 |
| IL7R | interleukin 7 receptor | −2.852 | 0.0004 | −2.062 | 0.0037 |
| CFB | complement factor B | −2.285 | 0.0013 | −2.067 | 0.003 |
| IFIH1 | interferon induced with helicase C domain 1 | −1.922 | 0.0014 | −2.099 | 0.0007 |
| CXCL8 | C-X-C motif chemokine ligand 8 | −2.298 | 0.0003 | −2.155 | 0.0005 |
| CD14 | CD14 molecule | −2.154 | 0.0039 | −2.286 | 0.0027 |
| STAT4 | signal transducer and activator of transcription 4 | −2.518 | 0.0002 | −2.315 | 0.0004 |
| IRF1 | interferon regulatory factor 1 | −3.253 | 0.0004 | −3.083 | 0.0006 |
| MMP7 | matrix metallopeptidase 7 | −3.358 | 0.0001 | −3.165 | 0.0002 |
| IL33 | interleukin 33 | −3.109 | 1.51E−05 | −3.314 | 1.96E−05 |
| OLFM4 | olfactomedin 4 | −6.772 | 2.66E−05 | −3.505 | 0.0003 |

In a typical method of improving an individual's vaginal microbiome, the method includes decreasing undesirable (nonbeneficial) microbial and/or fungal growth in an individual's vagina. Such methods generally include administering to the individual an amount of compound JWH-133 or L759,633 effective for modulating genes involved in microbial and/or fungal growth. Such genes may be involved in the immune response (e.g., innate immune response) to a particular microbe or fungus. For example, genes involved in the innate immune response that are up-regulated or by JWH-133 or L759,633 are shown in Table 1. Specifically, as mentioned above, up-regulation of the genes of Table 1 by JWH-133 or L759,633 can decrease undesirable bacterial, fungal and viral growth (e.g., by promoting or inducing a response against the undesirable bacteria, virus or fungus). Further regarding the methods described herein for increasing or promoting an immune response against a microbe or pathogen in an individual's vagina, Table 5 shows the upregulation of IFNE (interferon epsilon) by JWH-133 and L759,633 which can promote an immune response against viruses, particularly HIV. Thus, administering JWH-133 or L759,633 can reduce or inhibit viral growth in an individual's vagina.

As mentioned above, one embodiment of a method of modulating (i.e., improving) an individual's vaginal microbiome includes administering compound L759,633 or compound JWH-133 in an amount effective for increasing glycogen production, promoting Lactobacillus colonization, and decreasing pH in the individual's vagina. By administering compound JWH-133 or compound L759,633, the gene responsible for glycogen production, GYS2, is upregulated to a greater fold change than by administration of estradiol. In such methods, increasing glycogen production in the individual is beneficial for vaginal health because glycogen promotes Lactobacillus colonization in the vagina which produces lactic acid and lowers the pH which results in an unfavorable environment for the growth of pathogenic bacteria.

In some embodiments of a method of treating the GSM in an individual, the individual suffers from vaginal thinning and vaginal atrophy. In such an individual, administering JWH-133 or L759,633 may increase epidermal development and/or keratinocyte differentiation in the individual's vagina. Typically in such an embodiment, administering JWH-133 or L759,633 up-regulates one or more genes in Table 3 which results in increased epidermal development and/or keratinocyte differentiation and restoration of the vaginal tissue and alleviation or reversal of the vaginal atrophy in the individual. In some embodiments of a method of treating the GSM in an individual, the individual suffers from vaginal dryness. In such an individual, administering JWH-133 or L759,633 may increase moisture, lubrication and blood flow in the vagina by up-regulating one or more genes in Table 2.

The methods described herein can further include detecting a state or condition of the GSM (the presence of the GSM) in the individual. The detection is typically done prior to administering to the individual compound L759,633 or compound JWH-133, or a composition including either compound. For example, methods of treating the GSM in an individual, modulating an individual's vaginal microbiome, and increasing or decreasing expression of any one gene(s) from any one of Tables 1-9 as described herein may include a step of obtaining a sample from the individual and analyzing it to determine if the individual suffers from the GSM. Methods of detecting the GSM in an individual are well known in the art, and include: detection of atrophy of labia majora and minora; and detection of mucosa that appear pale, shiny and dry. As another example, detection of vaginal rugae disappearance and shortening and narrowing of the vagina which results in greater exposure of the urethral meatus may be used to detect the GSM. As another example, the pH may be measured and if greater than 4.6, it is indicative of VVA. A further example is use of the vaginal maturation index (VMI).

Any suitable methods of administering compound L759,633 or compound JWH-133 or a composition containing either compound to an individual may be used. In these methods, the compounds and compositions can be administered to an individual by any suitable route, e.g., oral, buccal (e.g., sublingual), parenteral (e.g., subcutaneous, intramuscular, intradermal, or intravenous), and topical (i.e., both skin and mucosal surfaces, administration. In an embodiment, compound L759,633 or compound JWH-133 or a composition containing either compound may be administered orally. In another embodiment, compound L759,633 or compound JWH-133 or a composition containing either compound may be administered sublingually. In another embodiment, compound L759,633 or compound JWH-133 or a composition containing either may be administered directly to a target site (e.g., vagina).

The therapeutic methods described herein in general include administration of a therapeutically effective amount of compound L759,633 or compound JWH-133 or a composition containing either compound to an individual (e.g., human female) in need thereof, particularly a human. Such treatment will be suitably administered to individuals, particularly humans, suffering from, having, susceptible to, or at risk for a disease, disorder, or symptom thereof (e.g., the GSM, VVA). Determination of those individuals "at risk" can be made by any objective or subjective determination by a diagnostic test or opinion of a subject or health care provider.

Effective Doses

Compounds L759,633 and JWH-133 and compositions containing either compound are preferably administered to an individual in need thereof (e.g., human female having the GSM) in an effective amount, that is, an amount capable of producing a desirable result in a treated individual. Desirable results include one or more of, for example, alleviation or reversal of VVA, reduced RUTI, alleviation of dyspareunia, alleviation or reversal of vaginal dryness, alleviation or elimination of vaginal irritation (e.g., pain), alleviation or elimination of vaginal itching, alleviation or elimination of incontinence, restoration of vaginal wall thickness, decreased vaginal pH, decreased risk of sexually transmitted disease, modification/attenuation of immune function, etc. Such a therapeutically effective amount can be determined according to standard methods. Toxicity and therapeutic efficacy of compounds L759,633 and JWH-133 and compositions containing these compounds can be determined by standard pharmaceutical procedures. As is well known in the medical and veterinary arts, dosage for any one individual depends on many factors, including the individual's size, body surface area, age, the particular composition to be administered, time and route of administration, general health, and other drugs being administered concurrently. A delivery dose of compound L759,633 or compound JWH-133 is determined based on preclinical efficacy and safety.

Kits

Described herein are kits for alleviating or treating the GSM in an individual. A typical kit includes a composition including compound L759,633 or compound JWH-133 and a pharmaceutically acceptable carrier, and instructions for use. Kits also typically include a container and packaging. Instructional materials for preparation and use of the kit components are generally included. While the instructional materials typically include written or printed materials, they are not limited to such. Any medium capable of storing such instructions and communicating them to an end user is encompassed by the kits herein. Such media include, but are not limited to electronic storage media and the like. Such media may include addresses to internet sites that provide such instructional materials.

EXAMPLES

The present invention is further illustrated by the following specific examples. The examples are provided for illustration only and should not be construed as limiting the scope of the invention in any way.

Example 1—Genes Involved in Vaginal Health and Function

Applying a previously used Affymetrix array to read epithelial cell gene expression in women who used *Lactobacillus rhamnosus* as a probiotic to treat bacterial vaginosis and its effects on their anti-microbial defenses, a study of 10 post-menopausal women filtered genes that were linked to the depletion of estrogen who reported vaginal dryness as a symptom of atrophy (Hummelen et al., PLoS One, vol. 6, no. 11, 2011). Hummulen et al. disclosed the top 20 genes up- and down-regulated ($p<0.05$) in their vaginal dryness group compared to controls. These 20 genes are listed below in Table 6:

TABLE 6

Genes Up- and Down-Regulated in Vaginal Dryness (Hummulen et al.)

| Gene Symbol | Gene Assignment | Ref Seq ID | Fold change |
|---|---|---|---|
| MMP7 | matrix metallopeptidase 7 (matrilysin, uterine) | NM_002423 | 13.75 |
| SLC44A4 | solute carrier family 44, member 4 | NM_025257 | 9.19 |
| SLC44A4 | solute carrier family 44, member 4 | NM_025257 | 9.19 |
| SLC44A4 | solute carrier family 44, member 4 | NM_025257 | 9.19 |
| CFH | complement factor H | NM_000186 | 8.72 |
| PIGR | polymeric immunoglobulin receptor | NM_002644 | 8.64 |
| IL19 | interleukin 19 Transcript ID: 8158684 Transcript ID: 8180303 | NM_153758 | 8.31, 8.28, 7.73 |
| CFB | complement factor B | NM_001710 | 7.33 |
| PLAT | plasminogen activator tissue Transcript ID: 8138487 | NM_000930 | 7.19, 7.10 |

TABLE 6-continued

Genes Up- and Down-Regulated in
Vaginal Dryness (Hummulen et al.)

| Gene Symbol | Gene Assignment | Ref Seq ID | Fold change |
|---|---|---|---|
| CFB | complement factor B | NM_001710 | 6.93 |
| WFDC2 | WAP four-disulfide core domain 2 | NM_006103 | 6.61 |
| CXCL6 | chemokine (C-X-C motif) ligand 6 | NM_002993 | 6.50 |
| TSPAN1 | tetraspanin 1 | NM_005727 | 6.30 |
| AGR2 | anterior gradient homolog 2 (*Xenopus laevis*) | NM_006408 | 6.18 |
| TRIM31 | tripartite motif-containing 31 | NM_007028 | 5.85 |
| ASS1 | argininosuccinate synthetase 1 | NM_000050 | 5.70 |
| PLAC8 | placenta-specific 8 | NM_016619 | 5.51 |
| SPINK7 | Serine peptidase inhibitor, Kazal type 7 (putative) | NM_032566 | −38.65 |
| TGM3 | transglutaminase 3 | NM_003245 | −21.86 |
| SBSN | Surprabasin, part of a gene complex including dermokine | NM_198538 | −20.93 |
| ALOX12 | arachidonate 12-lipoxygenase | NM_000697 | −19.61 |
| KPRP | keratinocyte proline-rich protein | NM_001025231 | −17.43 |
| GYS2 | glycogen synthase 2 (liver) | NM_021957 | −16.78 |
| DSG1 | desmoglein 1 | NM_001942 | −16.61 |
| LCE3E | late cornified envelope 3E | NM_178435 | −15.35 |
| LCE3D | late cornified envelope 3D | NM_032563 | −14.61 |
| SERPINB12 | serpin peptidase inhibitor, clade B | NM_080474 | −14.11 |
| PNLIPRP3 | pancreatic lipase-related protein 3 | NM_001011709 | −13.69 |
| KRTDAP | keratinocyte differentiation-associated protein | NM_207392 | −13.08 |
| CLDN17 | claudin 17 | NM_012131 | −12.88 |
| KRT1 | keratin 1 | NM_006121 | −11.99 |
| LOC441178 | hypothetical LOC441178 | AL832737 | −10.89 |
| LOC441178 | hypothetical LOC441178 | AL832737 | −10.89 |
| ME1 | malic enzyme 1, NADP(+)-dependent, cytosolic Transcript ID: 8020347 | NM_002395 | −10.57, −10.26 |
| CRCT1 | cysteine-rich C-terminal 1 | NM_019060 | −9.80 |
| CRISP3 | cysteine-rich secretory protein 3 | NM_006061 | −9.75 |

It was reported that there were 960 genes differentially expressed by at least 2-fold that were linked to changes in the transcription of genes associated with cellular structure and immune function. A GeneOntology (GO) enrichment analysis demonstrated changes in epithelial remodeling and immune response and that cornified envelope had the highest enrichment score (62.50%) and that 10 genes were downregulated in the dryness group. Since barrier function is dependent on other structural components such as adhesion molecules, keratin and arachidonate metabolism, their down-regulation would have a negative effect on the mechanical stability of the tissue and be a contributing factor to VVA (Toulza et al., Genome Biol, vol. 8, no. 6, 2007). The direct down-regulation by the loss of estrogen of claudin 17, suprabasin, keritnocyte proline-rich protein, desmoglein, transglutaminase 3 all of which are involved with the integrity of the junctional proteins would lead to the friability of the tissue and pain and bleeding with intercourse.

Since dryness is accompanied by inflammation, the up-regulation of molecules involved with the degradation of the extracellular matrix such as Matrilyisin-1 protein (MMP, aka matrix metallopeptidase), complement factor B (CFB) and complement factor H which not only leads to a dysregulated immune environment but also contributes to vaginal thinning. Furthermore, the recruitment of monocytes and leukocytes through the up-regulation of chemokines was also noted in the dryness group. Additionally, the up-regulation of the polymeric immunoglobulin receptor (PIGR) in the dryness group also points to an increased mucosal immune activity as a contributing factor in the dryness group. The increased expression of a gene involved with the uptake of choline in neurons (SLC44A4) could lead to the increased perception of pain through cholinergic nerve endings.

An analysis of gene array data obtained from the biopsies of 19 women being treated with 17β-estradiol (E2) for symptoms associated with VVA before and after treatment corroborated the previous findings showing that estradiol differentially regulated those very genes implicated in vaginal dryness (Cotreau et al., Maturitas, vol. 58, no. 4, pp. 366-376.2007). The epithelial proliferation which was noted in the E2 group was associated with the up-regulation of genes involved with keratin synthesis, keratinocyte differentiation and keratinization which would provide improved structural stability to the epithelium. Keratins further undergoes covalent cross-linking by E2 upregulated transglutaminases 1 and 3 to further improve the barrier function (Vijayalakshmi et al., Exp Cell Res, vol. 214, no. 1, pp. 358-366, 1994). The up-regulation of markers of terminally differentiated epithelial cells include small proline-rich region proteins 1, 2 and 3 (SPPR1-3) (Marshall et al. J Invest Dermatol, vol. 114, no. 5, pp. 967-975, 2000). A gene involved in cell-cell junction, desmosomal cadherin (desmoglein) DSG1 is also significantly upregulated by E2 and contributes to the overall barrier function of the vaginal tissue. The increased expression of VEGF promotes increased vascularity of the submucosal tissue which provides further support to the thickening of the epithelium. The positive effect which E2 has on both the innate and adaptive immune responses has been noted to provide defense against pathogens (Wira et al., Am J Reprod Immunol, vol. 53, no. 2, pp. 65-76, 2005). By the same token, the genes involved in immune cell recruitment to the vaginal environment which can lead to inflammation and exacerbate dryness are down regulated by E2.

Example 2—Microarray Analysis of Genes Involved in Vaginal Health and Function

In order to more fully understand the effects of compounds L759,633 and JWH-133 on the vaginal tissue construct with respect to increased tissue thickness and transepithelial resistance, a microarray analysis of 20,000 genes was done. The data from the Affymetrix Human Gene 1.0 ST arrays were normalized using the Robust Multiarray Average (RMA) algorithm and a Chip Definition File (CDF) that maps the probes on the array to unique Entrez Gene identifiers. The result is a matrix in which each column corresponds to a sample. The expression values are log 2-transformed by default.

By using a fold change >1.5, an analysis of differentially expressed genes was done to identify those genes which were involved in the cornified envelope, keratinocyte differentiation, cell differentiation, epidermis development, epithelial cell differentiation, junctional proteins and signaling, immune response and innate immune response.

Keratin and its associated proteins make up more than 80-90% of the protein mass of the epidermis. Although it has been demonstrated that hormones have little effect on the thickness of the epithelium before menopause, its thinning during and after menopause due to the lack of estrogen is the principle cause of VVA. Of the top 20 up- and down-regulated genes (p<0.05) in the vaginal dryness group compared to controls, compounds L759,633 and JWH-133 had the opposite effects on 10 of the top 20 up-regulated genes and on 15 of the top 20 down-regulated genes (see Table 7). Also see Table 6 above (Hummelen et al., PLoS One, vol. 6, no. 11, 2011) listing genes that were found to be up- and down-regulated in vaginal dryness.

TABLE 7

Differential Gene Expression in Vaginal Dryness
Differential Gene Expression in the Vaginal Dryness of
Menopause and the effects of the lead compounds

| | | Dryness | | L759,633 | | JWH-133 | |
|---|---|---|---|---|---|---|---|
| Symbol | Entrez Gene Name | Fold Change | p-value | Fold Change | p-value | Fold Change | p-value |
| MMP7 | matrix metallopeptidase 7 | 13.75 | 7.73E−03 | −3.3 | 2.20E−04 | −3.2 | 8.65−05 |
| SLC44A4 | solute carrier family 44, member 4 | 9.19 | 2.23E−02 | −2.7 | 3.40E−03 | −2 | 9.50E−04 |
| PIGR | polymeric immunoglobulin receptor | 8.64 | 2.01E−02 | −2.4 | 2.60E−03 | −1.8 | 2.60E−03 |
| IL19 | Interleukin 19 | 8.31 | 3.30E−02 | −3.5 | 8.40E−04 | −2.2 | 2.40E+02 |
| CFB | Complement Factor B | 7.33 | 4.69E−02 | −2.3 | 8.50E−04 | −2 | 1.30E−02 |
| WFDC2 | WAP four-disulfide core domain 2 | 6.61 | 8.32E−03 | −2.8 | 1.30E−06 | −2.6 | 7.40E−04 |
| TSPAN1 | Tetraspanin 1 | 6.3 | 2.42E−02 | −2.3 | 1.30E−03 | −1.9 | 3.50E−02 |
| AGR2 | Anterior gradient homolog 2 (*Xenopus laevis*) | 6.18 | 1.50E−02 | −3.1 | 2.10E−03 | −2.5 | 8.10E−03 |
| TRIM31 | Tripartite motif-containing 31 | 5.85 | 4.77E−02 | −5.9 | 9.50E−05 | −4.5 | 2.50E−02 |
| ASS1 | arginosuccinate synthetase 1 | 5.7 | 3.05E−03 | −2.8 | 7.80E−05 | −2.4 | 1.10E−02 |
| PLAC8 | placenta-specific 8 | 5.51 | 2.03E−02 | −3.3 | 1.30E−03 | −2.2 | 1.10E−02 |
| TGM3 | transglutamase 3 | −21.86 | 4.24E−05 | 30.1 | 4.50E−07 | 24 | 9.90E−06 |
| SBSN | Suprabasin, part of a gene complex including dermokine | −20.93 | 3.28E−05 | 4.3 | 5.70E−04 | 3.4 | 9.40E−04 |
| ALOX12 | arachidonate 12-lipoygenase | −19.61 | 3.28E−05 | 1.5 | 4.00E−03 | 1.8 | 9.50E−03 |
| KPRP | keratinocyte proline-rich protein | −17.43 | 2.30E−04 | 25.3 | 3.90E−07 | 20.8 | 3.70E−03 |
| GYS2 | glycogen synthase 2 (liver) | −16.78 | 1.66E−03 | 2.9 | 1.10E−04 | 3.1 | 8.00E−04 |
| DSG1 | desmoglein 1 | −16.61 | 5.02E−03 | 8.7 | 7.60E−04 | 7.2 | 1.50E−03 |
| LCE3E | late cornified envelope 3E | −15.35 | 6.78E−04 | 16 | 1.10E−04 | 13.5 | 6.10E−04 |
| LCE3D | late cornified envelope 3D | −14.61 | 3.27E−03 | 15.6 | 5.70E−05 | 12.6 | 4.80E−04 |
| SERPINB12 | serpin peptidase inhibitor, clade B | −14.11 | 1.42E−03 | 5.1 | 9.40E−04 | 4.3 | 1.30E−03 |
| PNLIPRP3 | pancreatic lipase-related protein 3 | −13.69 | 3.06E−04 | 1.6 | 1.20E−02 | 1.4 | 2.90E−02 |
| KRTDAP | keratinocyte differentiation-associated protein | −13.08 | 2.16E−03 | 15.7 | 9.20E−05 | 10.1 | 9.20E−05 |
| CLDN17 | claudin 17 | −12.88 | 1.99E−03 | 11 | 2.00E−04 | 8.7 | 5.20E−03 |
| KRT1 | keratin 1 | −11.99 | 1.16E−03 | 10.5 | 3.70E−04 | 8.7 | 5.20E−03 |
| ME1 | malic enzyme 1, NADP(+)-dependent cytosolic | −10.57 | 1.32E−03 | 2.9 | 2.20E−04 | 2.4 | 1.20E−03 |
| CRCT1 | cysteine-rich C-terminal 1 | −9.8 | 3.86E−03 | 2.6 | 1.20E−04 | 2.3 | 9.10E−04 |

Overall, six genes involved with keratin synthesis, keratinocyte differentiation and keratinization were differentially regulated by compounds estradiol, L759,633 and JWH-133-KRTDAP, KRT1, KRT23, KRT24, KRT2, and KRT20. Members of the small proline-rich region protein family which belong to a class of cornified envelope precursor proteins: SPRR2D, SPRR2G, SPRR4 are upregulated by the all three compounds and provide cross-linking to the keratin proteins. Proteins which have adhesive properties and provide additional cross-linking to the small proline-rich region protein family include corneodesmosin (CDSN), the transglutamases 3, 5 and 1 which are essential to the integrity of the epidemis and are significantly upregulated by estradiol and L759,633 and JWH-133. SBSN (suprabasin) and DMKN (dermokine) which are found in the stratum spinosum are upregulated by all three compounds (estradiol and L759,633 and JWH-133). SBSN is a substrate for TGM 2 and 3 activity and plays a role in the process of epidermal differentiation. (Park et al. J Biol Chem, vol. 277, no. 47, 2002, pp. 45195-45202). DMKN is a substrate for MMP10 (Schlage et al. Mol Cell Proteomics, vol. 14, no. 12, 2015, pp. 3234-3246) which is downregulated by L759,633. Dermokine may be involved with cell adhesion, proliferation and differentiation. Late cornified envelope proteins have a similar cross-linking function similar to SPRR and of the seven which are upregulated by L759,633 and JWH-133, only LCE2A, LCE2C/LCE2D and LCE2B are upregulated by estradiol. Another gene identified as a novel component of the cornified envelope is CNFN (cornifelin) which was up-regulated by L759,633 and JWH-133>1.5 fold where it was not by estradiol. It is found in the stratum *granulosum*, a transition layer in the epidermis and is cross-linked to LOR (loricrin). Likewise, LOR, which is a terminally differentiating structural protein comprising more than 70% of the cornified envelope is significantly upregulated by L759,633 and JWH-133 but is not by estradiol. DSG1 (desmoglein 1) and DSC1, DSC2 and DSC3 (desmocollin 1,2, and 3) are also upregulated by the cannabinoids but estradiol did not reach the 1.5 fold-change threshold for DSC2 and 1 and the desmocollins are types of transmembrane proteins known as desmosomal cadherins which form junctions between cells known as desmosomes which would therefore strengthen the tissue.

Genes involved with lipid metabolism in the keratinocyte provide integrity and cohesion to the stratum corneum. See Table 4 above. The overall trend towards upregulation suggests that these genes would be able to prevent the loss of water, solutes and proteins thereby preventing dryness as well as protect against invading pathogens. One of these genes that is involved in lipid metabolism, ALOX12B, was down-regulated in menopausal tissue by −4.53 fold and upregulated by 6.6 fold by compounds L759,633 and JWH-133. It is not only involved with epithelial development but in in the production of mucin which is essential to maintaining a protective layer to the mucosa as well as having a lubricating function. Although MUCL1 (mucin like 1) was the only gene that is involved with mucin production, it was up-regulated by L759,633 by almost 2 fold. Other factors involved with moisture and lubrication which would be of benefit to the woman experiencing the dryness and friability of the vaginal mucosa in the VVA syndrome of menopause, would be the increased production of filaggrin and filaggrin 2, major keratin-binding peptides which, in association with the transglutamases, aid in the bundling of the intermediate keratin filaments and the formation of the cornified envelope which is responsible for fortifying the barrier function. Filaggrin and filaggrin 2 (Riethmuller et al., J Allergy Clin Immunol, vol. 136, no. 6, pp. 1573-1580, e2.2015) also provide a natural moisturizing effect to the stratum corneum and prevent the escape of moisture from the epithelium (Wu et al., PLoS One, vol. 4, no. 4, 2009). Accordingly, the methods described herein include administering L759,633 or JWH-133 in an amount effective for increasing expression of any of these genes for increasing moisture and lubrication in an individual's vagina. See Table 2 for a list of genes that that according to the methods of the invention, are up-regulated by administration of compounds L759,633 and JWH-133 for treating the GSM.

Pruritis (itch) is a common symptom of VVA of menopause. Although histamine has been the classic molecule in mitigating itch, antagonists have not been effective against dry skin pruritis. The presence of vanilloid receptors (TRPV) (Steinhoff, M. & Biro, T. 2009, J Invest Dermatol, vol. 129, no. 3, pp. 531-535) in keratinocytes and sensory nerve endings represents a novel target for the treatment of vaginal pruritis of menopause. Although the exact mechanism for the upregulation of the TRPV3 gene by L759,633 and JWH-133 by 2.8 and 2.32 fold, respectively, is not known, they may be ligands for the receptor itself similar to other cannabinoids (Muller et al. Front Mol Neurosci, vol. 11, 2018, p 487) and act in concert with other molecules which are either up or down-regulated by the treatment.

An immune response to the presence of pathogens is necessary for the prevention of local tissue damage and the systemic consequences of an infection transmitted across mucosal surfaces. An excessive and unlimited response would result in local tissue damage and promote the deleterious effects observed in the VVA of menopause. The expression of both IL36A and its antagonist IL36RN suggest that a limitation on the inflammatory response is established with the treatment of the vaginal tissue by estradiol and L759,633 and JWH-133 This down-regulation of the immune response in the senescent vagina would have the benefit of decreasing inflammation by lowering immune cell recruitment. Other genes showing a response in common with all three treatments (estradiol, L759,633 and JWH-133) are noted below in Table 8. However, the upregulation of GSF2RB (colony stimulating factor 2 receptor beta common subunit) would provide the benefit of recruiting neutrophils and macrophages to the vaginal mucosa in response to the presence of bacterial pathogens. Likewise the upregulation of CD244 could influence the activity of both NK cells and dendritic cells in response to pathogens presenting on the apical surface of the vaginal epithelium thereby limiting the infection. Additionally, both L759,633 and JWH-133 upregulated NCR3LG1 (natural killer cell cytoxicity receptor 3 ligand 1) would contribute to NK activation and cytotoxicity. On the other hand, the down-regulation of HLA-DRA by all three compounds would limit the immune response and act in an anti-inflammatory fashion by preventing antigen processing. Interestingly, estradiol was only able to down-regulate four of the HLA subtypes (HLA-DMB, HLA-DPA1, HLA-DMA and HLA-DRA) whereas L759,633 was able to down-regulate an additional three molecules (HLA-C, HLA-B and HLA-DRB6) while JWH-133 was only able to downregulate only HLA-DRA and HLA-B. See Table 9 below listing HLA genes. While the complement system is intrinsically related to the innate immune response, its unchecked expression can lead to continued inflammation (Calippe et al., 2017 'Complement Factor H Inhibits CD47-Mediated Resolution'; Rajeevan et al., Hum Immunol, vol. 76, no. 8, pp. 553-560, 2015). It has been noted that the upregulation of CFB and CFH have been implicated in vaginal dryness and thinning associated with VVA of menopause (Hummelen et al., PLoS One, vol. 6, no. 11, 2011). Both L759,633 and JWH-133 were able to down-regulate CFH by 1.769 and 1.681 fold and CFB by 2.285 and 2.167 fold respectively.

TABLE 8

Immune Response Genes in Common With All Three Treatments

| Symbol | Entrez Gene Name | Estradiol Expr Fold Change(A3) | Estradiol Expr False Discovery Rate (q-value)(A3) | L759,633 Expr Fold Change(A2) | L759,633 Expr False Discovery Rate (q-value)(A2) | JWH-633 Expr Fold Change(A1) | JWH-633 Expr False Discovery Rate (q-value)(A1) |
|---|---|---|---|---|---|---|---|
| IL36A | interleukin 36 alpha | 3.409 | 1.43E−05 | 4.185 | 6.8E−06 | 4.253 | 9.11E−06 |
| IL36RN | interleukin 36 receptor antagonist | 2.751 | 0.0003 | 4.668 | 1.17E−05 | 4.029 | 0.0000221 |
| CSF2RB | colony stimulating factor 2 receptor beta common subunit | 1.517 | 0.0055 | 2.79 | 1.33E−05 | 2.595 | 0.0000246 |
| CD244 | CD244 molecule | 2.355 | 0.0035 | 2.837 | 0.0003 | 2.489 | 0.0009 |
| IL23A | interleukin 23 subunit alpha | 2.912 | 0.0001 | 2.677 | 5.78E−05 | 2.346 | 0.0002 |
| IL1R2 | interleukin 1 receptor type 2 | 2.966 | 0.0014 | 2.799 | 0.0005 | 1.922 | 0.0087 |
| CD74 | CD74 molecule | −1.89 | 0.0066 | −2.103 | 0.001 | −1.676 | 0.0092 |
| HLA-DRA | major histocompatibility complex, class II, DR alpha | −2.234 | 0.0021 | −2.792 | 0.0001 | −1.875 | 0.0031 |
| TNFRSF10C | TNF receptor superfamily member 10c | −2.162 | 0.0004 | −2.458 | 4.56E−05 | −2.114 | 0.0002 |
| CCL28 | C-C motif chemokine ligand 28 | −1.948 | 0.0028 | −2.504 | 0.0001 | −2.39 | 0.0002 |
| FYB1 | FYN binding protein 1 | −2.225 | 0.005 | −2.604 | 0.0006 | −2.398 | 0.0012 |
| TLR3 | toll like receptor 3 | −2.081 | 0.0033 | −3.274 | 0.000059 | −2.566 | 0.0003 |
| VTCN1 | V-set domain containing T cell activation inhibitor 1 | −2.364 | 0.0074 | −4.666 | 8.24E−05 | −2.694 | 0.0014 |

TABLE 9

Histocompatibility Complex Genes

| Symbol | Entrez Gene Name | Estradiol Expr Fold | Estradiol Expr False Discovery Rate (q-value)(A3) | E759,633 Expr Fold Change(A2) | E759,633 Expr False Discovery Rate (q-value)(A2) | JWH-633 Expr Fold Change(A1) | JWH-633 Expr False Discovery Rate (q-value)(A1) |
|---|---|---|---|---|---|---|---|
| HLA-DRB6 | major histocompatibility complex, class II, DR beta 6 (pseudogene) | −2.5 | 1.4E−01 | −2.7 | 6.10E−02 | −1.5 | 3.0−01 |
| HLA-DRA | major histocompatibility complex, class II, DR alpha | −2.234 | 0.0021 | −2.792 | 0.0001 | −1.875 | 0.0031 |
| HLA-DPA1 | major histocompatibility complex, class II, DP alpha 1 | −1.8 | 1.20E−01 | −1.7 | 5.50E−02 | N/A | |

TABLE 9-continued

Histocompatibility Complex Genes

| | | Estradiol | | E759,633 | | JWH-633 | |
|---|---|---|---|---|---|---|---|
| Symbol | Entrez Gene Name | Expr Fold | Expr False Discovery Rate (q-value)(A3) | Expr Fold Change(A2) | Expr False Discovery Rate (q-value)(A2) | Expr Fold Change(A1) | Expr False Discovery Rate (q-value)(A1) |
| HLA-B | major histocompatibility complex, class I, B | N/A | | −2.168 | 0.0006 | −1.677 | 0.0073 |
| HLA-C | major histocompatibility complex, class C | N/A | | −1.691 | 0.0018 | −1.5 | 2.00E−02 |
| HLA-DMB | major histocompatibility complex, class II, DM beta | N/A | | −1.591 | 0.0001 | N/A | |

Many of the above-noted genes are differentially regulated by estradiol in menopausal tissue. Although not hormones, compounds L759,633 and JWH-133 have an even greater effect on barrier function than estradiol. With respect to the barrier function, only 6% of macrophages which had been cultured with the tissue for four hours in the presence of TNF-α were capable of infiltrating into the tissue past 90 um (vs. 28% into the untreated tissue, p<0.006 ANOVA). The estrogen treatment showed a similar effect, but not as dramatic (16% vs 28%) compared to negative controls (see FIG. 1). This would indicate that the increased gene expression of the proteins involved with cross-linking of the keratin fibers, filagrins and desmosomal cadherins are all contributing to the fortification of the vaginal mucosa which would prevent the infiltration of pathogens and prevent the loss of solutes and water from within the tissue. Accordingly, the methods described herein include administering L759,633 or JWH-133 in an amount effective for increasing expression of any of these genes.

As mentioned in Example 1, the up-regulation of the SLC44A4 gene found in the vaginal atrophy group would lead to increased pain sensation through the increased uptake of choline by the parasympathetic nerve endings which are found in the vaginal tissue. The down-regulation of this gene by −2.7 fold by compound L759,633 would lead to the opposite and beneficial effects. Compound JWH-133 also causes a downregulation of this gene (a −1.978 fold change). Accordingly, the methods described herein include administering L759,633 or JWH-133 in an amount effective for downregulating the SLC44A4 gene, e.g., in an individual suffering from vaginal atrophy and/or pain.

Since the stratum corneum is devoid of nucleated cells as part of the terminal differentiation process, the production of glycogen would have to take place in the lower layers of the epithelium where the translational machinery is still intact. The presence of free glycogen in the genital fluid is supportive of *Lactobacillus* colonization which is important to genital health since the metabolism of glycogen yields lactic acid which lowers the pH of the vagina. The up-regulation of glycogen synthase 2 gene would clearly contribute to the health of the vaginal tissue as was noted by its up-regulation in the estradiol and the cannabinoid treated tissue.

The loss of blood supply to the vaginal area contributes to its thinning but the up-regulation of the vascular endothelial growth factor (VEGFA) gene by E2 and compounds L759,633 and JWH-133 would clearly contribute to the neovascularization in the vagina. The vasodilatory effects that L759,633 and JWH-133 will have on the blood flow in the senescent vagina will be the result of the upregulation of the TRPV3 gene which will increase the number of vallinoid receptors in the tissue and the nerve endings and smooth muscle of the arterial and venous blood vessels. Accordingly, the methods described herein include administering L759,633 or JWH-133 in an amount effective for upregulating VEGFA and TRPV3.

Another gene whose up-regulation would have benefit in the setting of the GSM which is marked by RUTI is RNASE7, which produces a protein which has natural antimicrobial properties. Accordingly, the methods described herein include administering L759,633 or JWH-133 in an amount effective for upregulating RNASE7, e.g., in an individual suffering from RUTI.

Example 3—Effects of Compounds L759,633 and JWH-133 on Gene Expression

Although both L759,633 and JWH-133 are highly selective ligands for the CB2 receptor, L759,633 had a greater effect on expression of some genes than JWH-133. The tissues were treated for seven days with the administration of compounds L759,633 and JWH-133 to the culture medium which suggests that compounds L759,633 and JWH-133 can be taken orally in any pharmaceutically acceptable formulation. Compounds L759,633 and JWH-133 could also be taken sublingually, by strips to allow for buccal absorption or by spray. Compounds L759,633 and JWH-133 could also be administered by nasal spray or topically to the skin in the form of a gel, cream, ointment or specially designed patch for the delayed and hence prolonged absorption of compounds L759,633 and JWH-133.

Example 4—Compounds JWH-133 and L759,633 are more effective than Estradiol in the comparison of the overall fold change of the expression of genes involved in the dryness of vaginal tissue during menopause. See Tables 6 and 7.

Example 5—Upregulation of VEGFA by Compound L759,633

VEGFA (vascular endothelial growth factor A) was upregulated by estradiol and L759,633 by 2.2. and 2.0 fold, respectively. The upregulation of the VEGFA gene by estradiol and L759,633 by 2.2 and 2.0 fold respectively leads to the proliferation and migration of endothelial cells, i.e. the vascularization (angiogenesis) in the individual's vagina suffering from VVA of menopause. Blood flow will be increased as a result of the upregulation of the TRPV3 gene which leads to the increased expression of the vallinoid receptor in the smooth muscle of blood vessels and the nerve endings which innervate them.

Other Embodiments

Any improvement may be made in part or all of the compounds, compositions, and method steps. All references, including publications, patent applications, and patents, cited herein are hereby incorporated by reference. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contraindicated by context.

What is claimed is:

1. A method of treating genitourinary syndrome of menopause in an individual comprising administering to the individual a composition comprising a pharmaceutically acceptable carrier and a therapeutically effective amount of:
    i) a compound having the formula:

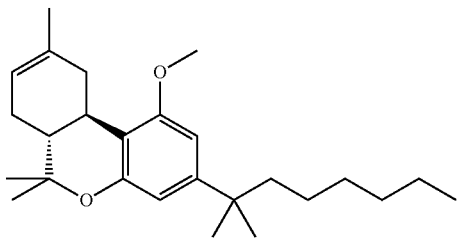 [SMILES: CCCCCCC(C)(C)c1cc(OC)c2c(c1)OC(C)(C)[C@@H]1CC=C(C)C[C@@H]21]

or
    ii) a compound having the formula:

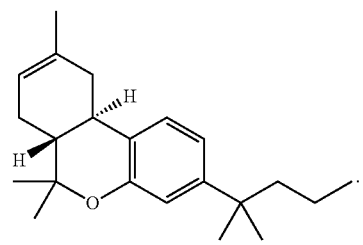 [SMILES: CCCC(C)(C)c1ccc2c(c1)OC(C)(C)[C@@H]1CC=C(C)C[C@@H]21]

2. The method of claim 1, wherein the genitourinary syndrome of menopause comprises at least one of: vulvovaginal atrophy, vaginal dryness, prurutis, incontinence, dyspareunia, and recurrent urinary tract infections, and administration of the composition ameliorates at least one of: vulvovaginal atrophy, vaginal dryness, incontinence, dyspareunia, and recurrent urinary tract infections in the individual.

3. The method of claim 2, wherein the individual has vulvovaginal atrophy resulting from loss of estrogen during perimenopause and/or menopause.

4. The method of claim 2, wherein the individual has vulvovaginal atrophy resulting from surgical removal of ovaries.

5. The method of claim 2, wherein the individual has vulvovaginal atrophy resulting from the use of aromatase inhibitors during treatment of breast cancer.

6. The method of claim 1, wherein the therapeutically effective amount is an amount sufficient to increase mucin production in the individual's vagina, increase keratin fiber synthesis and keratin fiber cross-linking in the individual's vagina, decrease cytokine, chemokine and matrix metalloproteinas expression in the individual's vagina, and increase vascularization and blood flow in the individual's vagina.

7. The method of claim 1, wherein the individual is a human.

8. The method of claim 1, wherein the composition further comprises an estrogen steroid hormone.

9. A method of modulating an individual's vaginal microbiome comprising administering to the individual a composition comprising a pharmaceutically acceptable carrier and a therapeutically effective amount of:
    i) a compound having the formula:

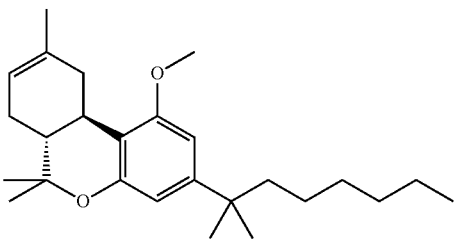 [SMILES: CCCCCCC(C)(C)c1cc(OC)c2c(c1)OC(C)(C)[C@@H]1CC=C(C)C[C@@H]21]

or
    ii) a compound having the formula:

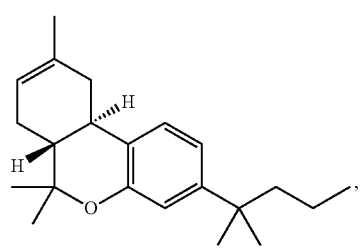

wherein the therapeutically effective amount is an amount effective for at least one of: increasing glycogen production for promoting *Lactobacillus* colonization and decreasing pH in the individual's vagina, increasing RNAase7 expression for anti-bacterial activity, and increasing NLRP10 expression for anti-fungal activity.

10. The method of claim 9, wherein the individual has at least one of: vulvovaginal atrophy, vaginal dryness, incontinence, dyspareunia, and recurrent urinary tract infections.

11. The method of claim 10, wherein the individual has vulvovaginal atrophy resulting from loss of estrogen during perimenopause and/or menopause.

12. The method of claim 10, wherein the individual has vulvovaginal atrophy resulting from surgical removal of ovaries.

13. The method of claim 10, wherein the individual has vulvovaginal atrophy resulting from the use of aromatase inhibitors during and after treatment of breast cancer.

14. The method of claim 9, wherein the individual is a human.

* * * * *